(12) United States Patent
Weiss

(10) Patent No.: US 11,174,303 B2
(45) Date of Patent: Nov. 16, 2021

(54) SINGLE-CHAIN INSULIN ANALOGUES STABILIZED BY A FOURTH DISULFIDE BRIDGE

(71) Applicant: Case Western Reserve University, Cleveland, OH (US)

(72) Inventor: Michael A. Weiss, Indianapolis, IN (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/492,824

(22) PCT Filed: Mar. 7, 2018

(86) PCT No.: PCT/US2018/021331
§ 371 (c)(1),
(2) Date: Sep. 10, 2019

(87) PCT Pub. No.: WO2018/165290
PCT Pub. Date: Sep. 13, 2018

(65) Prior Publication Data
US 2020/0140517 A1    May 7, 2020

Related U.S. Application Data

(60) Provisional application No. 62/468,037, filed on Mar. 7, 2017.

(51) Int. Cl.
*A61K 38/28* (2006.01)
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC ..................................................... C07K 14/62
See application file for complete search history.

(56) References Cited

U.S. PATENT DOCUMENTS 6,620,890 B1    9/2003   Yamashita et al.

FOREIGN PATENT DOCUMENTS

| WO | 2010/0080609 | 7/2010 |
| WO | 2015/0106269 | 7/2015 |
| WO | 2017/0112952 | 6/2017 |

OTHER PUBLICATIONS

Hua, Q. et al., "Design of an Active Ultrastable Single-Chain Insulin Analog Synthesis, Structure, and Therapeutic Implications," The Journal of Biological Chemistry, 2008, vol. 283, No. 21, pp. 14703-14716.

*Primary Examiner* — Gyan Chandra
(74) *Attorney, Agent, or Firm* — Hahn Loeser & Parks, LLP; John J. Cunniff

(57) ABSTRACT

A single-chain insulin analogue comprises a B-chain insulin polypeptide connected to an A-chain insulin polypeptide by a C-domain polypeptide. The B-chain insulin polypeptide contains a Cysteine substitution at position B4. The A-chain insulin polypeptide contains a Cysteine substitution at position A10. The C-domain polypeptide is 4 to 11 amino acids long. The analogue mitigates the unfavorable activity of this 4th disulfide bridge in conventional two-chain insulin analogues resulting in a duration of insulin signaling similar to that of wild-type insulin. A method of treating a patient with diabetes mellitus comprises the administration of a physiologically effective amount of the protein or a physiologically acceptable salt thereof to a patient. Use of a single-chain insulin analogue of the present invention in an insulin delivery device (such as a pump or pen) or as part of a high-temperature polymer-melt manufacturing process.

18 Claims, 8 Drawing Sheets
Specification includes a Sequence Listing.

PROINSULIN

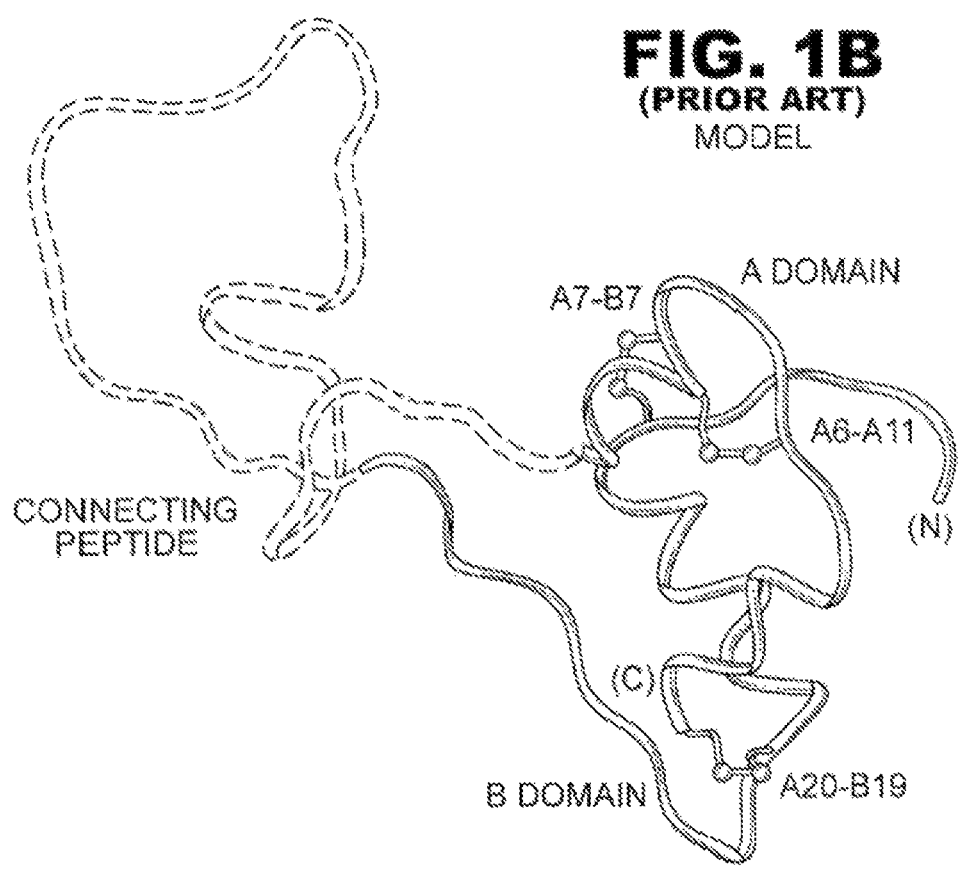

SEQUENCE LISTING

```
<160> NUMBER OF SEQ ID NOS: 32

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens
```

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 62
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position
<220> FEATURE:
<221> NAME/KEY: misc_feature
<222> LOCATION: (29)..(29)
<223> OTHER INFORMATION: Xaa is Glu, Ala, Ile, Leu, Val, Norleucine,
      amino propionic acid or amino butryic acid
<220> FEATURE:
<221> NAME/KEY: misc_feature
<222> LOCATION: (31)..(41)
<223> OTHER INFORMATION: Xaa is 4-11 of any amino acid wherein at least
      one of (31) and (32) are Asp or Glu
<220> FEATURE:
<221> NAME/KEY: misc_feature
<222> LOCATION: (49)..(49)
<223> OTHER INFORMATION: Xaa is His, Glu, Lys, Arg, Gly, Ser, Cys, Asn,
      Asp Tyr, or Gln
<220> FEATURE:
<221> NAME/KEY: misc_feature
<222> LOCATION: (55)..(55)
<223> OTHER INFORMATION: Xaa is Tyr, Gly, Ser, Cys, Gln, Asn, Lys, Arg,
      His, Asp or Glu
<220> FEATURE:
<221> NAME/KEY: misc_feature
<222> LOCATION: (62)..(62)
<223> OTHER INFORMATION: Xaa is Asn, Gly, Ala, Asp, Glu or Ser

<400> SEQUENCE: 4

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30

Xaa Xaa Xaa Xaa Xaa Xaa Xaa Xaa Xaa Gly Ile Val Glu Gln Cys Cys
        35                  40                  45

Xaa Ser Cys Cys Ser Leu Xaa Gln Leu Glu Asn Tyr Cys Xaa
    50                  55                  60

<210> SEQ ID NO 5
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg,
      Norleucine, amino propionic acid or amino butryic acid
<220> FEATURE:
<221> NAME/KEY: MISC_FEATURE
<222> LOCATION: (44)..(44)
<223> OTHER INFORMATION: Xaa is His, Glu, Tyr, Gln, Lys, Arg, Gly, Ser,
      Cys, Asn or Asp
<220> FEATURE:

<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 5

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 6
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg,
      Norleucine, amino propionic acid or amino butryic acid
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 6

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Ala
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 7
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg,
      Norleucine, amino propionic acid or amino butryic acid
<220> FEATURE:
<221> NAME/KEY: MISC_FEATURE
<222> LOCATION: (44)..(44)

```
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 7

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Ala Glu
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 8
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg,
      Norleucine, amino propionic acid or amino butryic acid
<220> FEATURE:
<221> NAME/KEY: MISC_FEATURE
<222> LOCATION: (34)..(34)
<223> OTHER INFORMATION: Xaa is Pro, Ala, Ser or Glu
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 8

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Gly Xaa Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 9
<211> LENGTH: 57
<212> TYPE: PRT
<213> ORGANISM: Artificial Sequence
<220> FEATURE:
<223> OTHER INFORMATION: synthetic construct
<220> FEATURE:
```

<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg, Norleucine, amino propionic acid or amino butyric acid
<220> FEATURE:
<221> NAME/KEY: MISC_FEATURE
<222> LOCATION: (34)..(34)
<223> OTHER INFORMATION: Xaa is Pro, Ala, Ser or Glu
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser, Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg, His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 9

Phe Val Asn Cys His Leu Cys Gly Ser His Leu Val Glu Ala Leu Tyr
 1               5                  10                  15

Leu Val Cys Gly Glu Arg Gly Phe Phe Tyr Thr Pro Xaa Thr Glu Ala
            20                  25                  30

Gly Xaa Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 10
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg, Norleucine, amino propionic acid or amino butyric acid
<220> FEATURE:
<221> NAME/KEY: MISC_FEATURE
<222> LOCATION: (34)..(34)
<223> OTHER INFORMATION: Xaa is Pro, Ala, Ser or Glu
<220> FEATURE:
<221> NAME/KEY: MISC_FEATURE
<222> LOCATION: (35)..(35)
<223> OTHER INFORMATION: Xaa is Ala, Ser, Gly, Glu, Gln, or Lys
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser, Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg, His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 10

Phe Val Asn Cys His Leu Cys Gly Ser His Leu Val Glu Ala Leu Tyr
 1               5                  10                  15

Leu Val Cys Gly Glu Arg Gly Phe Phe Tyr Thr Pro Xaa Thr Glu Ala
            20                  25                  30

```
Gly Xaa Xaa Arg Gly Ile Val Glu Gln Cys Cys Xaa Ser Cys Cys Ser
         35                  40                  45

Leu Xaa Gln Leu Glu Asn Tyr Cys Xaa
     50                  55

<210> SEQ ID NO 11
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Asp, Ile, Leu, Val, Lys, Arg,
      Norleucine, amino propionic acid or amino butryic acid
<220> FEATURE:
<221> NAME/KEY: MISC_FEATURE
<222> LOCATION: (34)..(34)
<223> OTHER INFORMATION: Xaa is Pro, Ala, Ser or Glu
<220> FEATURE:
<221> NAME/KEY: MISC_FEATURE
<222> LOCATION: (36)..(36)
<223> OTHER INFORMATION: Xaa is Ala, Ser, Gly, Glu, Gln, or Lys
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 11

Phe Val Asn Cys His Leu Cys Gly Ser His Leu Val Glu Ala Leu Tyr
 1               5                  10                  15

Leu Val Cys Gly Glu Arg Gly Phe Phe Tyr Thr Pro Xaa Thr Glu Ala
             20                  25                  30

Gly Xaa Arg Xaa Gly Ile Val Glu Gln Cys Cys Xaa Ser Cys Cys Ser
         35                  40                  45

Leu Xaa Gln Leu Glu Asn Tyr Cys Xaa
     50                  55

<210> SEQ ID NO 12
<211> LENGTH: 62
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa is Phe or a modification of Phe by a
      halogen atom (F, Cl or Br) at the ortho or 2 ring position
<220> FEATURE:
<221> NAME/KEY: MISC_FEATURE
<222> LOCATION: (28)..(28)
<223> OTHER INFORMATION: Xaa indictes Gln, Glu, Ala, Asn, Asp, Ile, His,
      Leu, Val, ornithine, di amino propionic acid or di amino butryic
      acid
<220> FEATURE:
<221> NAME/KEY: MISC_FEATURE
<222> LOCATION: (31)..(41)
<223> OTHER INFORMATION: Xaa is 4-11 of any amino acid wherein at least
      one of (31) and (32) are Asp or Glu
```

```
<220> FEATURE:
<221> NAME/KEY: MISC_FEATURE
<222> LOCATION: (49)..(49)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (55)..(55)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (62)..(62)
<223> OTHER INFORMATION: Xaa is Asn, Gly, Ala, Asp, Glu or Ser

<400> SEQUENCE: 12

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Xaa Pro Thr Xaa Xaa
            20                  25                  30

Xaa Xaa Xaa Xaa Xaa Xaa Xaa Xaa Xaa Gly Ile Val Glu Gln Cys Cys
        35                  40                  45

Xaa Ser Cys Cys Ser Leu Xaa Gln Leu Glu Asn Tyr Cys Xaa
    50                  55                  60

<210> SEQ ID NO 13
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 13

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 14
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
```

```
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (44)..(44)
<223> OTHER INFORMATION: Xaa is His, Tyr, Gln,Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 14

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Ala
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 15
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 15

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Ala Glu
            20                  25                  30

Gly Pro Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 16
<211> LENGTH: 57
<212> TYPE: PRT
<213> ORGANISM: Artificial Sequence
<220> FEATURE:
```

<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (34)..(34)
<223> OTHER INFORMATION: Xaa is Pro or Ser
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa  is Gly, Glu, Ala, Asn, Asp or Ser

<400> SEQUENCE: 16

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Xaa Arg Arg Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 17
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (34)..(34)
<223> OTHER INFORMATION: Xaa is Pro or Ser
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 17

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Ala
            20                  25                  30

Gly Xaa Arg Arg Gly Ile Val Glu Gln Cys Cys Xaa Ser Cys Cys Ser

Leu Xaa Gln Leu Glu Asn Tyr Cys Xaa
    50              55

<210> SEQ ID NO 18
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (34)..(34)
<223> OTHER INFORMATION: Xaa is Arg, Pro or Ser
<220> FEATURE:
<221> NAME/KEY: MISC_FEATURE
<222> LOCATION: (35)..(35)
<223> OTHER INFORMATION: Xaa is Arg or Ser
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 18

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Ala
            20                  25                  30

Gly Xaa Xaa Arg Gly Ile Val Glu Gln Cys Cys Xaa Ser Cys Cys Ser
        35                  40                  45

Leu Xaa Gln Leu Glu Asn Tyr Cys Xaa
    50              55

<210> SEQ ID NO 19
<211> LENGTH: 57
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (28)..(28)
<223> OTHER INFORMATION: Xaa is Gln, Glu, Ala, Asn, Asp, Ile, His, Leu,
      Val, ornithine, di amino propionic acid or di amino butryic acid
<220> FEATURE:
<221> NAME/KEY: MISC_FEATURE
<222> LOCATION: (34)..(34)
<223> OTHER INFORMATION: Xaa is Arg, Pro or Ser
<220> FEATURE:
<221> NAME/KEY: MISC_FEATURE
<222> LOCATION: (36)..(36)
<223> OTHER INFORMATION: Xaa is Arg, Pro or Ser
<220> FEATURE:
<221> NAME/KEY: MISC_FEATURE
<222> LOCATION: (44)..(44)
<223> OTHER INFORMATION: Xaa is His, Tyr, Gln, Glu, Lys, Arg, Gly, Ser,
      Cys, Asn or Asp

```
<220> FEATURE:
<221> NAME/KEY: MISC_FEATURE
<222> LOCATION: (50)..(50)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (57)..(57)
<223> OTHER INFORMATION: Xaa is Gly, Glu, Ala, Asn, Asp or Ser

<400> SEQUENCE: 19

Phe Val Asn Cys His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Ala
            20                  25                  30

Gly Xaa Arg Xaa Gly Ile Val Glu Gln Cys Cys Xaa Ser Cys Cys Ser
        35                  40                  45

Leu Xaa Gln Leu Glu Asn Tyr Cys Xaa
    50                  55

<210> SEQ ID NO 20
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position
<220> FEATURE:
<221> NAME/KEY: MISC_FEATURE
<222> LOCATION: (29)..(29)
<223> OTHER INFORMATION: Xaa indictes Arg or Lys
<220> FEATURE:
<221> NAME/KEY: MISC_FEATURE
<222> LOCATION: (46)..(46)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (52)..(52)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (59)..(59)
<223> OTHER INFORMATION: Xaa is Asn, Gly, Ala, Asp, Glu or Ser

<400> SEQUENCE: 20

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Xaa Thr Glu Glu
            20                  25                  30

Gly Ser Arg Arg Ser Arg Gly Ile Val Glu Gln Cys Cys Xaa Ser Cys
        35                  40                  45

Cys Ser Leu Xaa Gln Leu Glu Asn Tyr Cys Xaa
    50                  55

<210> SEQ ID NO 21
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
```

```
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position

<400> SEQUENCE: 21

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Arg Thr Glu Glu
            20                  25                  30

Gly Ser Arg Arg Ser Arg Gly Ile Val Glu Gln Cys Cys Arg Ser Cys
        35                  40                  45

Cys Ser Leu Tyr Gln Leu Glu Asn Tyr Cys Gly
    50                  55

<210> SEQ ID NO 22
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position

<400> SEQUENCE: 22

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Arg Thr Glu Ala
            20                  25                  30

Gly Ser Arg Arg Ser Arg Gly Ile Val Glu Gln Cys Cys Arg Ser Cys
        35                  40                  45

Cys Ser Leu Tyr Gln Leu Glu Asn Tyr Cys Gly
    50                  55

<210> SEQ ID NO 23
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position

<400> SEQUENCE: 23

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Arg Thr Ala Glu
            20                  25                  30

Gly Ser Arg Arg Ser Arg Gly Ile Val Glu Gln Cys Cys Arg Ser Cys
        35                  40                  45

Cys Ser Leu Tyr Gln Leu Glu Asn Tyr Cys Gly
    50                  55

<210> SEQ ID NO 24
<211> LENGTH: 59
<212> TYPE: PRT
```

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa is Phe, Leu, cyclohexanylalanine or a
      modification of Phe by a halogen atom (F, Cl or Br) at the ortho
      or 2 ring position

<400> SEQUENCE: 24

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Arg Thr Glu Glu
            20                  25                  30

Gly Pro Arg Arg Ser Arg Gly Ile Val Glu Gln Cys Cys Arg Ser Cys
        35                  40                  45

Cys Ser Leu Tyr Gln Leu Glu Asn Tyr Cys Gly
        50                  55

<210> SEQ ID NO 25
<211> LENGTH: 55
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa indictes Glu, Ala, Ile, Leu, Val,
      Norleucine, amino propionic acid or amino butryic acid
<220> FEATURE:
<221> NAME/KEY: MISC_FEATURE
<222> LOCATION: (42)..(42)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (48)..(48)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (55)..(55)
<223> OTHER INFORMATION: Xaa is Gly, Glu, Ala, Asn, Asp or Ser

<400> SEQUENCE: 25

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Arg Arg Gly Ile Val Glu Gln Cys Cys Xaa Ser Cys Cys Ser Leu Xaa
        35                  40                  45

Gln Leu Glu Asn Tyr Cys Xaa
        50                  55

<210> SEQ ID NO 26
<211> LENGTH: 56
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Ile, Leu, Val, Norleucine,
      amino propionic acid or amino butryic acid
<220> FEATURE:
<221> NAME/KEY: MISC_FEATURE
```

```
<222> LOCATION: (43)..(43)
<223> OTHER INFORMATION: Xaa is His, Try, Gln, Glu, Lys, Arg, Gly, Ser,
      Cys, Asn or Asp
<220> FEATURE:
<221> NAME/KEY: MISC_FEATURE
<222> LOCATION: (49)..(49)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (56)..(56)
<223> OTHER INFORMATION: Xaa is Gly, Glu, Ala, Asn, Asp or Ser

<400> SEQUENCE: 26

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
                20                  25                  30

Gly Arg Arg Gly Ile Val Glu Gln Cys Cys Xaa Ser Cys Cys Ser Leu
            35                  40                  45

Xaa Gln Leu Glu Asn Tyr Cys Xaa
    50                  55

<210> SEQ ID NO 27
<211> LENGTH: 56
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Ile, Leu, Val, Norleucine,
      amino propionic acid or amino butryic acid
<220> FEATURE:
<221> NAME/KEY: MISC_FEATURE
<222> LOCATION: (43)..(43)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (49)..(49)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (56)..(56)
<223> OTHER INFORMATION: Xaa is Gly, Glu, Ala, Asn, Asp or Ser

<400> SEQUENCE: 27

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
                20                  25                  30

Ala Arg Arg Gly Ile Val Glu Gln Cys Cys Xaa Ser Cys Cys Ser Leu
            35                  40                  45

Xaa Gln Leu Glu Asn Tyr Cys Xaa
    50                  55

<210> SEQ ID NO 28
<211> LENGTH: 56
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Gly, Glu, Ala, Asn, Asp or Ser
```

```
<220> FEATURE:
<221> NAME/KEY: MISC_FEATURE
<222> LOCATION: (43)..(43)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (49)..(49)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (56)..(56)
<223> OTHER INFORMATION: Xaa is Gly, Glu, Ala, Asn, Asp or Ser

<400> SEQUENCE: 28

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Ser Arg Arg Gly Ile Val Glu Gln Cys Cys Xaa Ser Cys Cys Ser Leu
        35                  40                  45

Xaa Gln Leu Glu Asn Tyr Cys Xaa
    50                  55

<210> SEQ ID NO 29
<211> LENGTH: 56
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (29)..(29)
<223> OTHER INFORMATION: Xaa is Glu, Ala, Ile, Leu, Val, Norleucine,
      amino propionic acid or amino butryic acid
<220> FEATURE:
<221> NAME/KEY: MISC_FEATURE
<222> LOCATION: (43)..(43)
<223> OTHER INFORMATION: Xaa is His, Tyr, Gln, Glu, Lys, Arg, Gly, Ser,
      Cys, Asn or Asp
<220> FEATURE:
<221> NAME/KEY: MISC_FEATURE
<222> LOCATION: (49)..(49)
<223> OTHER INFORMATION: Xaa is Tyr, Gly, Ser, Cys, Gln, Asn, Lys, Arg,
      His, Asp or Glu
<220> FEATURE:
<221> NAME/KEY: MISC_FEATURE
<222> LOCATION: (56)..(56)
<223> OTHER INFORMATION: Xaa is Gly, Glu, Ala, Asn, Asp or Ser

<400> SEQUENCE: 29

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
            20                  25                  30

Pro Arg Arg Gly Ile Val Glu Gln Cys Cys Xaa Ser Cys Cys Ser Leu
        35                  40                  45

Xaa Gln Leu Glu Asn Tyr Cys Xaa
    50                  55

<210> SEQ ID NO 30
<211> LENGTH: 59
<212> TYPE: PRT
<213> ORGANISM: Artificial Sequence
<220> FEATURE:
<223> OTHER INFORMATION: synthetic construct

<400> SEQUENCE: 30
```

```
Phe Val Asn Cys His Leu Cys Gly Ser His Leu Val Glu Ala Leu Tyr
1               5                   10                  15
Leu Val Cys Gly Glu Arg Gly Phe Phe Tyr Thr Pro Arg Thr Glu Glu
                20                  25                  30
Gly Ser Arg Arg Ser Arg Gly Ile Val Glu Gln Cys Cys Arg Ser Cys
            35                  40                  45
Cys Ser Leu Tyr Gln Leu Glu Asn Tyr Cys Asn
        50                  55
```

<210> SEQ ID NO 31
<211> LENGTH: 57
<212> TYPE: PRT
<213> ORGANISM: Artificial Sequence
<220> FEATURE:
<223> OTHER INFORMATION: synthetic construct

<400> SEQUENCE: 31

```
Phe Val Asn Cys His Leu Cys Gly Ser His Leu Val Glu Ala Leu Tyr
1               5                   10                  15
Leu Val Cys Gly Glu Arg Gly Phe Phe Tyr Thr Asp Pro Thr Glu Glu
                20                  25                  30
Gly Pro Arg Arg Gly Ile Val Glu Gln Cys Cys His Ser Cys Cys Ser
            35                  40                  45
Leu Glu Gln Leu Glu Asn Tyr Cys Asn
        50                  55
```

<210> SEQ ID NO 32
<211> LENGTH: 57
<212> TYPE: PRT
<213> ORGANISM: Artificial Sequence
<220> FEATURE:
<223> OTHER INFORMATION: synthetic construct

<400> SEQUENCE: 32

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Asp Pro Thr Glu Glu
                20                  25                  30
Gly Pro Arg Arg Gly Ile Val Glu Gln Cys Cys His Ser Ile Cys Ser
            35                  40                  45
Leu Glu Gln Leu Glu Asn Tyr Cys Asn
        50                  55
```

SINGLE-CHAIN INSULIN ANALOGUES STABILIZED BY A FOURTH DISULFIDE BRIDGE

CROSS REFERENCE TO RELATED APPLICATIONS

This application is a national stage application of PCT/US2018/021331, filed on Mar. 7, 2018, which claims benefit of U.S. Provisional Application No. 62/468,037, filed on Mar. 7, 2017. The disclosures of the above-referenced applications are incorporated herein by reference.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

BACKGROUND OF THE INVENTION

This invention relates to polypeptide hormone analogues that exhibit enhanced pharmaceutical properties, such as increased thermodynamic stability, augmented resistance to thermal fibrillation above room temperature, decreased mitogenicity, and/or altered pharmacokinetic and pharmacodynamic properties, i.e., conferring more prolonged duration of action or more rapid duration of action relative to soluble formulations of the corresponding wild-type human hormone. More particularly, this invention relates to insulin analogues consisting of a single polypeptide chain that contains a novel class of foreshortened connecting (C) domains between A and B domains. The single-chain insulin analogues of the present invention may optionally contain standard or non-standard amino-acid substitutions at other sites in the A or B domains.

The engineering of non-standard proteins, including therapeutic agents and vaccines, may have broad medical and societal benefits. Naturally-occurring proteins—as encoded in the genomes of human beings, other mammals, vertebrate organisms, invertebrate organisms, or eukaryotic cells in general—often confer multiple biological activities. A potential benefit of non-standard proteins would be to achieve augmented resistance to degradation at or above room temperature, facilitating transport, distribution, and use. An example of a therapeutic protein is provided by insulin. Wild-type human insulin and insulin molecules encoded in the genomes of other mammals bind to insulin receptors in multiple organs and diverse types of cells, irrespective of the receptor isoform generated by alternative modes of RNA splicing or by alternative patterns of post-translational glycosylation. Wild-type insulin also binds with lower affinity to the homologous Type 1 insulin-like growth factor receptor (IGF-1R).

An example of a further medical benefit would be optimization of the stability of a protein toward unfolding or degradation. Such a societal benefit would be enhanced by the engineering of proteins more refractory than standard proteins with respect to degradation at or above room temperature for use in regions of the developing world where electricity and refrigeration are not consistently available. Analogues of insulin consisting of a single polypeptide chain and optionally containing non-standard amino-acid substitutions may exhibit superior properties with respect to resistance to thermal degradation or decreased mitogenicity. The challenge posed by its physical degradation is deepened by the pending epidemic of diabetes mellitus in Africa and Asia. Because fibrillation poses the major route of degradation above room temperature, the design of fibrillation-resistant formulations may enhance the safety and efficacy of insulin replacement therapy in such challenged regions.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure.

Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). A variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard one-letter code), the chain and sequence position (typically as a superscript).

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. Insulin exhibits an increase in degradation rate of 10-fold or more for each 10° C. increment in temperature above 25° C.; accordingly, guidelines call for storage at temperatures <30° C. and preferably with refrigeration. Fibrillation of basal insulin analogues formulated as soluble solutions at pH less than 5

(such as Lantus® (Sanofi-Aventis), which contains an unbuffered solution of insulin glargine and zinc ions at pH 4.0) also can limit their shelf lives due to physical degradation at or above room temperature; the acidic conditions employed in such formulations impairs insulin self-assembly and weakens the binding of zinc ions, reducing the extent to which the insulin analogues can be protected by sequestration within zinc-protein assemblies.

Insulin is also susceptible to chemical degradation, involving the breakage of chemical bonds with loss of rearrangement of atoms within the molecule or the formation of chemical bonds between different insulin molecules. Such changes in chemical bonds are ordinarily mediated in the unfolded state of the protein, and so modifications of insulin that augment its thermodynamic stability also are likely to delay or prevent chemical degradation. Insulin is also susceptible to physical degradation. The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the two-chain insulin molecule to increase or decrease the risk of fibrillation is highly unpredictable. Models of the structure of the insulin molecule envisage near-complete unfolding of the three-alpha helices (as seen in the native state) with parallel arrangements of beta-sheets formed successive stacking of B-chains and successive stacking of A-chains; native disulfide pairing between chains and within the A-chain is believed to be retained. Such parallel cross-beta sheets are thought to require substantial separation between the N-terminus of the A-chain and C-terminus of the B-chain (>30 Å), termini ordinarily in close proximity in the native state of the insulin monomer (<10 Å). Marked resistance to fibrillation of single-chain insulin analogues with foreshortened C-domains is known in the art and thought to possibly reflect a topological incompatibility between the splayed structure of parallel cross-beta sheets in an insulin protofilament and the structure of a single-chain insulin analogue with native disulfide pairing in which the foreshortened C-domain constrains the distance between the N-terminus of the A-chain and C-terminus of the B-chain to be unfavorable in a protofilament.

Globular proteins may in general be stabilized through the introduction an engineered disulfide bridge between paired sites of cysteine substitution. Application of this approach to two-chain analogues of human insulin (i.e., conventional insulin analogues) has been described with paired Cys substitutions at positions B4 and A10. The resulting constrained insulin analogue (containing a $4^{th}$ disulfide bridge) exhibited enhanced resistance to fibrillation (as probed in wells of a plate assay on shaking at high frequency in the presence of fluorescent probe Thioflavin T). This insulin analogue with an additional disulfide bond has increased stability. Although the analogue retains biological activity, its duration of action on intravenous bolus injection is abnormally prolonged relative to the duration of action of wild-type insulin. The essential observation was that a single intravenous injection of such an analogue (within the framework of des-B30-human insulin) in a diabetic rat leads to a sustained reduction in the blood-glucose concentration for several hours. Such prolongation of insulin action presumably occurs at the cellular level in target tissues; i.e., the variant hormone-receptor complex continues to function as an activated tyrosine kinase for a sustained period, leading to prolonged activation of post-receptor signaling pathways—possibly including sustained residence of the glucose transporter GLUT4 on the surface of the responding cell. This abnormal property of the insulin analogue stabilized by cystine B4-A10 is undesirable in a therapeutic insulin analogue formulation because (i) rapid-acting (or "prandial") insulin analogue formulations are designed to be absorbed and cleared rapidly from a subcutaneous depot with foreshortening of any "tail" of insulin action to avoid late-postprandial hypoglycemia; and (ii) sustained signaling by any insulin analogue (whether rapid-acting or basal) raises the risk of increased mitogenicity and carcinogenesis as illustrated by studies of $Asp^{B10}$-insulin. The increased mitogenicity and carcinogenesis of $Asp^{B10}$-insulin has been attributed to its prolonged residence time on the insulin receptor and on the homologous Type 1 IGF receptor (IGF-1R).

It would be desirable, therefore, for a single-chain insulin analogue to contain Cysteine substitutions at positions B4 and A10 such that, on folding, the resulting protein contains a $4^{th}$ disulfide bridge (cystine B4-A10) and that at least a portion of the glucose-lowering effect of wild-type insulin is retained without abnormal prolongation of this glucose-lowering effect. More generally, there is a need for an insulin analogue that displays increased thermodynamic stability and increased resistance to fibrillation above room temperature without conferring increased risk of hypoglycemia due to prolonged insulin action in lowering the blood-glucose concentration and without risk of carcinogenesis due to prolonged insulin signaling at the cellular level.

SUMMARY OF THE INVENTION

It is, therefore, an aspect of the present invention to provide single-chain insulin analogues that contain pairwise Cys substitutions at position B4 together with A10, with both positions being relative to the corresponding positions of wild-type insulin. It is an additional aspect of the present invention that absolute in vitro affinities of the single-chain insulin analogue for IR-A and IR-B are in the range 5-100% relative to wild-type human insulin and so does not exhibit prolonged residence times in the hormone-receptor complex relative to wild-type insulin. The present invention addresses the utility of single-chain insulin analogues in which the unfavorable effects of cysteine B4-10 on the duration of insulin signaling are mitigated by the engineered C domain, specifically, the introduction of novel foreshortened C domains of length 6-11 residues in place of the 36-residue wild-type C domain characteristic of human proinsulin.

The present invention harnesses the augmented stability conferred upon insulin by cystine B4-A10 without suffering from the disadvantages of abnormally prolonged and potentially dangerous insulin signaling at the same time. While it was believed that the conformational constraint introduced by the $4^{th}$ disulfide bridge reduces conformational fluctuations in the protein, mitigation of the prolonged-signaling problem would be expected by introducing substitutions or modifications that enhance conformational fluctuations elsewhere in the protein molecule. In this way, a balance might be achieved whereby the net effect of the combined modifications upon the dynamics of the insulin analogue and functional properties of the hormone-receptor complex would be reduced, i.e., through the cancellation of stabilizing and destabilizing interactions. Surprisingly however, the present invention provides an insulin analogue containing cystine B4-A10 that restores signaling duration similar to native insulin analogue through the introduction of a second stabilizing element, rather than a counter destabilizing element, namely, a foreshortened C domain between the B domain (B chain) and A domain (A chain). The invention provides, therefore, a novel single-chain insulin analogue.

In general, the present invention provides a single-chain insulin analogue comprising a B-chain insulin polypeptide sequence connected to an A-chain insulin polypeptide sequence by a C-domain polypeptide sequence. The B-chain insulin polypeptide sequence contains a Cysteine substitution at position B4. The A-chain insulin polypeptide sequence contains a Cysteine substitution at position A10. The C-domain polypeptide sequence is 4 to 11 amino acids long. The single-chain insulin analogue may be used in the manufacture of a medicament, such as one used to treat diabetes mellitus or other condition requiring the lowering of the blood sugar level of the patient. The present invention also provides a method of treating a patient with diabetes mellitus which comprises the administration of a physiologically effective amount of the single-chain insulin analogue or a physiologically acceptable salt thereof to a patient. The single-chain insulin analogue of the present invention may be used in an insulin delivery device such as an insulin pump or pen, or as part of a high-temperature polymer-melt manufacturing process.

BRIEF DESCRIPTION OF THE SEVERAL VIEWS OF THE DRAWINGS

FIG. 1B is a structural model of proinsulin, consisting of an insulin-like moiety and a disordered connecting peptide (dashed line).

DETAILED DESCRIPTION OF THE INVENTION

Figure 1A:
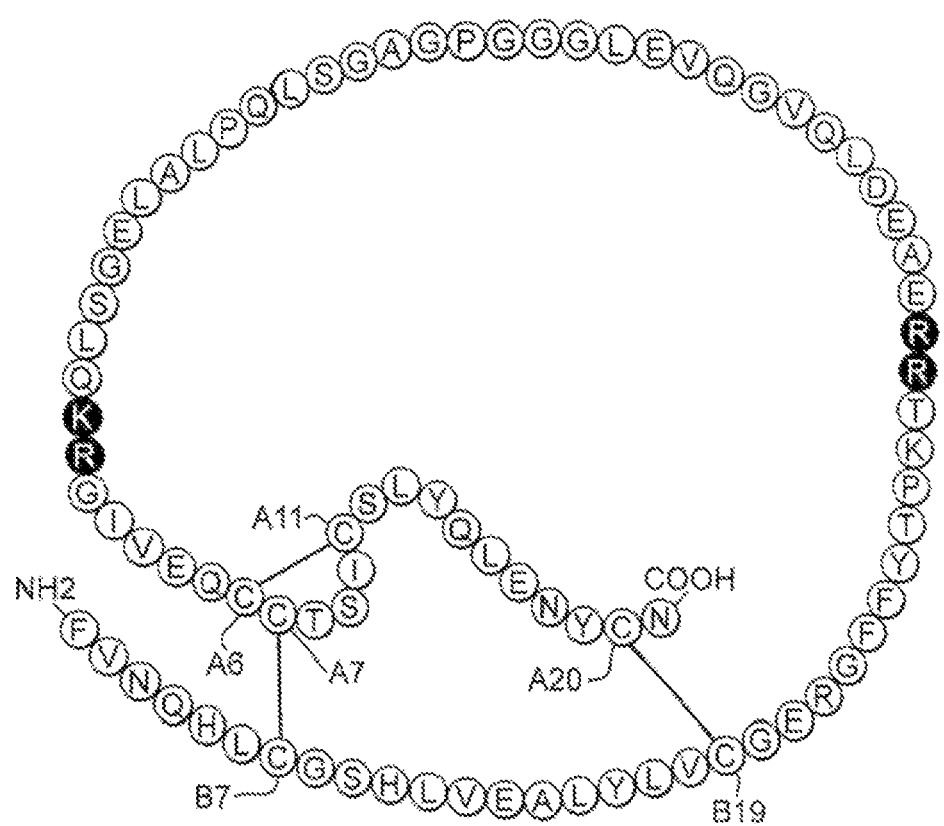
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1C:
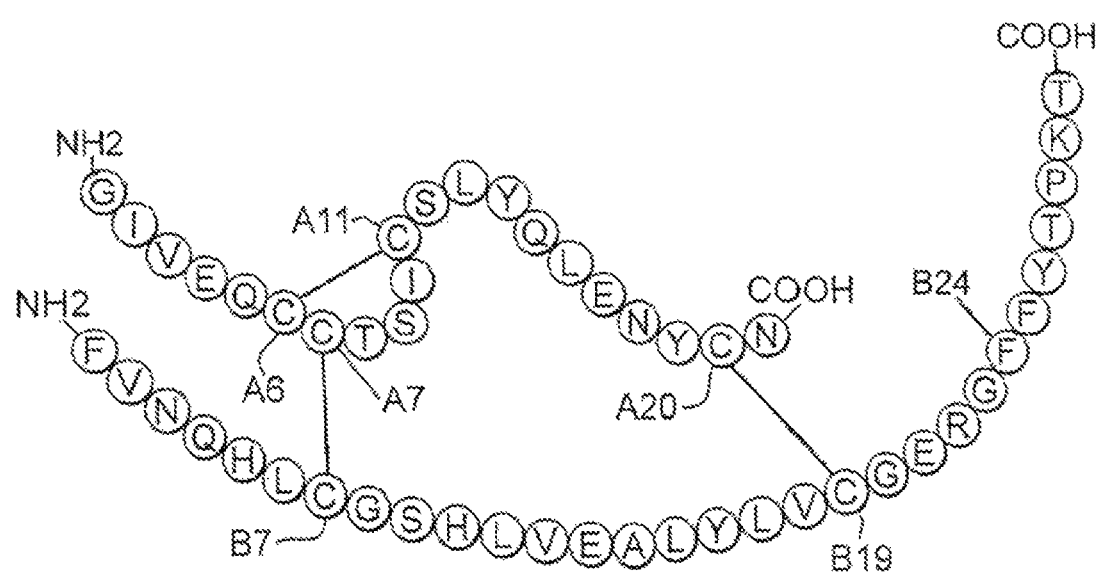
FIG. 1C is a schematic representation of the sequence of human insulin indicating the position of residues A6, A7, A11 and A20 in the A-chain (SEQ ID NO: 2) and B7, B19 and B24 in the B-chain (SEQ ID NO: 3).

The present invention is directed toward a single-chain insulin analogue that provides (i) enhanced stability and resistance to fibrillation due to the presence of a 4$^{th}$ disulfide bridge (cystine B4-A10) and yet (ii) avoids the abnormal prolongation of signaling associated with this modification in the framework of conventional two-chain insulin analogues. The single-chain insulin analogues of the present invention may have an isoelectric point between 4.0 and 6.0 (and so be suitable for formulation under neutral pH conditions as a rapid-acting insulin analogue formulation) or may have an isoelectric point between 6.5 and 8.0 (and so be suitable for formulation under acidic pH conditions as a basal insulin analogue formulation).

The present invention provides a single-chain insulin analogue that comprises a B-chain insulin polypeptide sequence connected to an A-chain insulin polypeptide sequence by a C-domain polypeptide sequence. The B-chain insulin polypeptide sequence contains a Cysteine substitution at position B4. The A-chain insulin polypeptide sequence contains a Cysteine substitution at position A10. The C-domain polypeptide sequence is 4 to 11 amino acids long. In some examples, the single-chain insulin comprises SEQ ID NO: 8, provided below.

The claimed invention includes a C-domain polypeptide comprising an N-terminal acid element, that is, one or more amino acids with acidic side chains. In some examples, the C-domain polypeptide of the single-chain insulin analogue of the present invention begins with Glu-Glu on the N-terminal end. In other examples, the C-domain polypeptide comprises residues 31-36 of SEQ ID NO: 31. In one particular example, the single-chain insulin analogue comprises SEQ ID NO: 31. In other examples, the C-domain polypeptide comprises residues 31-38 of SEQ ID NO: 30. In another particular example, the single-chain insulin analogue comprises SEQ ID NO: 30.

The claimed invention includes a C-domain polypeptide comprising a C-terminal basic element, that is, one or more amino acids with basic side chains. In some examples of the claimed invention, the C-domain polypeptide ends with Arg-Arg. In still other examples, the C-domain polypeptide ends with Arg-Arg-Ser-Arg. In further examples, the C-domain polypeptide ends with Ser-Arg-Arg-Ser-Arg.

The claimed invention also includes DNA or other nucleic acid sequences that encode the single-chain insulin analogues of SEQ ID NOs: 4-31.

The claimed invention further provides a method of treating a patient with diabetes mellitus which comprises the administration of a physiologically effective amount of the single-chain insulin analogue or a physiologically acceptable salt thereof to a patient. Accordingly, the single-chain insulin analogue of the present invention may be used as a medicament or for the manufacture of a medicament for the lowering of the blood sugar of a patient, such as a patient with diabetes mellitus. The single-chain insulin analogue of the present invention may be used in an insulin delivery device such as an insulin pump or pen, or as part of a high-temperature polymer-melt manufacturing process.

The single-chain insulin analogue may be formulated to contain zinc ions at a molar ratio of between 2 and 10 zinc ions per six single-chain insulin analogue monomers and the pH of the formulation may be between pH 3.0 and pH 4.5. The single-chain insulin analogue may be formulated to contain zinc ions at a molar ratio of between 0 and 3 zinc ions per six single-chain insulin analogue monomers and the pH of the formulation may be between pH 6.5 and pH 8.0. It is envisioned that the single-chain insulin analogue may be formulated at a strength of U-100, U-200, U-300, U-400, U-500 or even as high as U-1000.

The invention will be better understood by reference to the following examples which are included for the purpose of illustration and not limitation. Two molecular embodiments of this strategy were prepared by biosynthetic expression in the yeast *Pichia pastoris*, designated SCI-1 and SCI-2. These candidates differ in isoelectric point (pI) and hence in their pH-dependent solubilities: SCI-1 resembles insulin glargine in that it exhibits prolonged PK on conventional SQ injection whereas SCI-2 resembles insulin lispro in that it exhibits rapid onset of action on SQ injection.

Details of the SCI sequences are as follows. Each contains Cys at positions B4 and A10 in addition to the canonical Cys residues at positions B7, B19, A6, A7, A11 and A20. The C-domain linker sequences differ to simultaneously enable pI tuning and impair binding to the mitogenic IGF Type 1 receptor (IGF-1R). Each A domain contains a stabilizing non-β-branched substitution of $Thr^{48}$, an "Achilles' heel" in human insulin. SCI-1 (SEQ ID NO: 30; 59 residues; 8-residue C domain of sequence Glu-Glu-Gly-Ser-Arg-Arg-Ser-Arg) thus contains $Arg^{48}$ (whose positive charge contributes to its pI shift) whereas SCI-2 (SEQ ID NO: 31; 57 residues; 6-residue C domain of sequence Glu-Glu-Gly-Pro-Arg-Arg) contains $His^{48}$. While not wishing to condition patentability on theory, these variant side chains may interact with the side-chain carboxylate of $Glu^{44}$ to provide a favorable C-cap of the A1-A8 α-helix. SCI-1 contains the substitutions $Pro^{B28}$-$Arg^{B29}$ and SCI-2 contains substitutions $Asp^{B28}$-$Pro^{B29}$ (which impairs dimerization and hence can contribute to rapid absorption after subcutaneous injection)). Lysine (present at B29 in WT insulin and at B28 in lispro) was avoided to prevent cleavage in *P. pastoris* by a lysine-directed protease. Substitution of hyper-exposed $Tyr^{A14}$ by Glu it thought to mitigate an unfavorable "reverse-hydrophobic effect" and possibly removes a potential aromatic site of chemical degradation. Neither SCI-1 nor SCI-2 contain the substitution $His^{B10}$→Asp, which has been associated with enhanced mitogenicity in cell culture and carcinogenesis in rat testing. The sequences of SCI-1 and SCI-2 are otherwise derived from human insulin and are reflected in SEQ ID NOs: 30 and 31, respectively. Analogous synthetic genes have been prepared and cloned in *Pichia pastoris* encoding SCI-1 and derivatives of SCI-2.

The C-domain sequence in SCI-1 (EEG<u>SRRSR</u>, residues 31-38 of SEQ ID NO: 30) wherein the acidic element (positions C1 and C2; bold) was introduced in an attempt to impair binding to IGF-1R, Gly (position C3; italics) was introduced as a flexible joint, and an IGF-II C-domain-derived element (positions C4-C8 in the present analog; underlined) was employed in an attempt to reduce immunogenicity and possibly to enhance receptor binding. The formal isoelectric point (pI) of SCI-1 was predicted to be shifted toward neutrality by the combined effects of the C-domain sequence (three additional Arginine residues partially offset by two additional Glutamic acid residues) and an additional titratable Histidine at position A8; the substitution of Arg for Lys at B29 was expected to have a negligible effect on the isoelectric point. The isoelectric point of SCI-2 (in the range 4.0-5.0) is by contrast predicted to be similar to or lower than that of wild-type insulin and so is amenable to formulation at or near neutral pH in the presence or absence of zinc ions.

In view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Di-aminobutyric acid, or Di-aminopropionic acid). Lys may also be replaced by the neutral aliphatic isostere Norleucine (Nle), which may in turn be substituted by analogues containing shorter aliphatic side chains (Aminobutyric acid or Aminopropionic acid).

Figure 2:
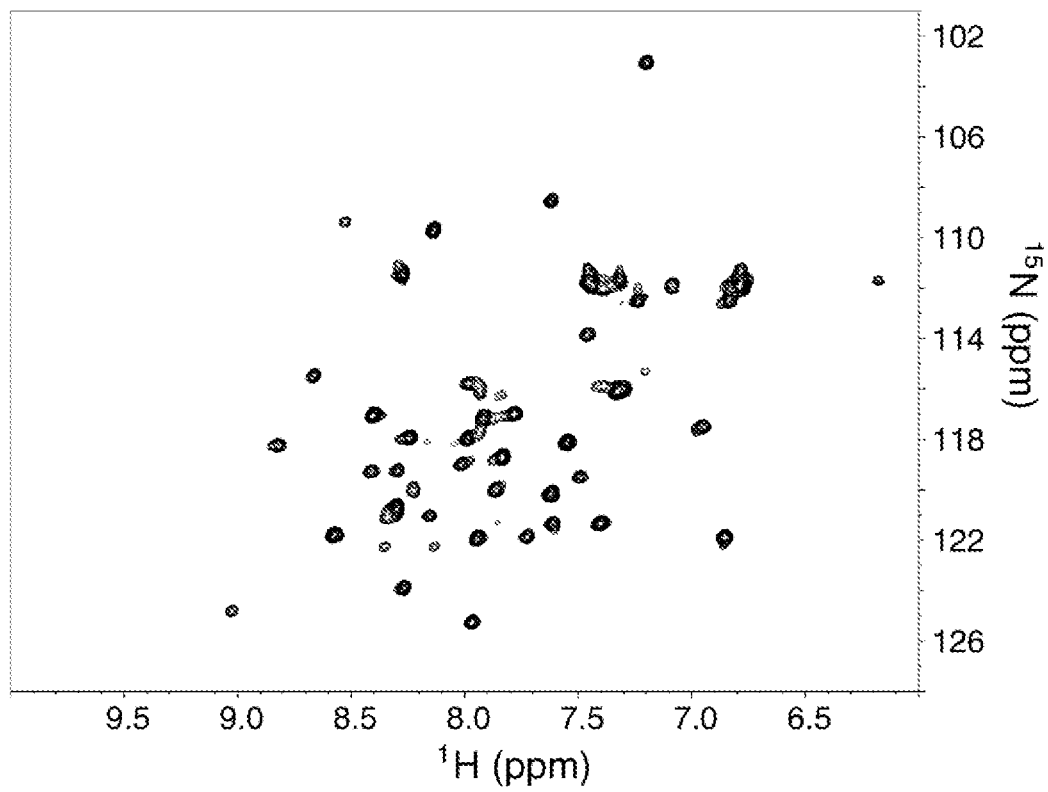
FIG. 2 provides the 2D $^1$H-$^{15}$N NMR spectrum of a single-chain insulin analogue SCI-2 of the present invention. The spectrum was acquired at pH 7 (as in a prandial formulation) and 37° C.

The 2D $^1H$-$^{15}N$ NMR "fingerprint" spectrum of SCI-2 uniformly labeled with $^{15}N$ (and with $^{13}C$) is provided evidence for a folded structure (FIG. 2).

To evaluate the biological activity, potency, duration of signaling, and thermal stability of the analogues in an animal model, male Sprague-Dawley rats (mean body mass ~300 grams) were rendered diabetic by treatment with streptozotocin (STZ). Protein solutions containing KP-insulin (insulin Lispro, the active component of Humalog®), insulin Glargine (Lantus®; Sanofi-Aventis), and/or a single-chain insulin of the present invention. A control was provided by injection of protein-free Lilly diluent (obtained from Eli Lilly and Co.) composed of 16 mg glycerin, 1.6 mg metacresol, 0.65 mg phenol, and 3.8 mg sodium phosphate pH 7.4. The activity of SCI-1 was evaluated in relation to that of Humalog® (U-100 strength taken from an unexpired commercial vial). SCI-1 was formulated according to the formulation of insulin Glargine in Lantus® except that the pH was adjusted in near 3.5. One unit of each of these formulations (or the equivalent in nanomoles of protein as units have not formally been defined for the analogues of the present invention) and injected IV, and resulting changes in blood glucose concentration were monitored by serial measurements using a clinical glucometer (Hypoguard Advance Micro-Draw meter). Rats were injected subcutaneously at time t=0 in groups of four (N=4). Blood was obtained from the clipped tip of the tail at time 0 and every 10 minutes up to 360 min. SCI-1 of the present invention was found, under conditions of formulation similar to that of Lantus®, to retain a substantial proportion of the biological activity of wild-type insulin, insulin lispro, or insulin glargine.

Figure 3A:
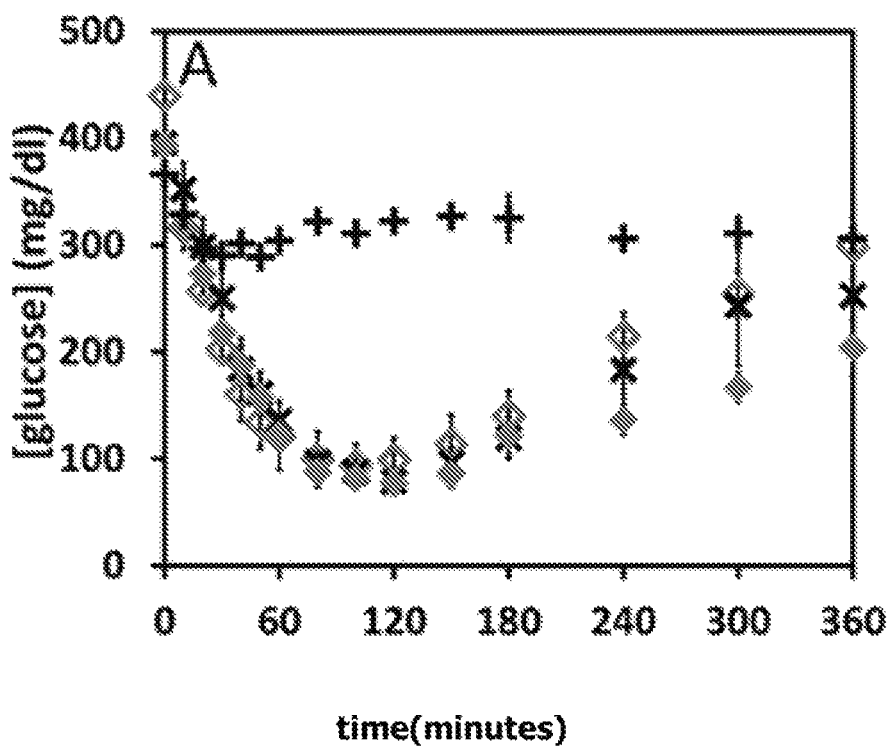
FIG. 3A is a graph of mean blood-glucose concentrations over time in Sprague-Dawley rats made diabetic with streptozotocin after IV bolus injection of fresh or heat-stressed SCI not containing a fourth disulfide bridge (SCI-1 without 4SS; SEQ ID NO: 32), or fresh or heat stressed Lantus® (N=4; mean glycemia ca. 400 mg/dl). Heat stressed insulin was given gentle agitation at 95° C. for 30 min. Doses for SCIs (nominally 1 IU/rat IV) were calculated in equivalent nanomoles protein/µl. Symbols: (✚) Lantus, 95° C. for 30 min; (✖) fresh Lantus; (◇) SCI-1 without 4SS, 95° C. for 30 min; and (◆) fresh SCI-1 without 4SS.
Figure 3B:
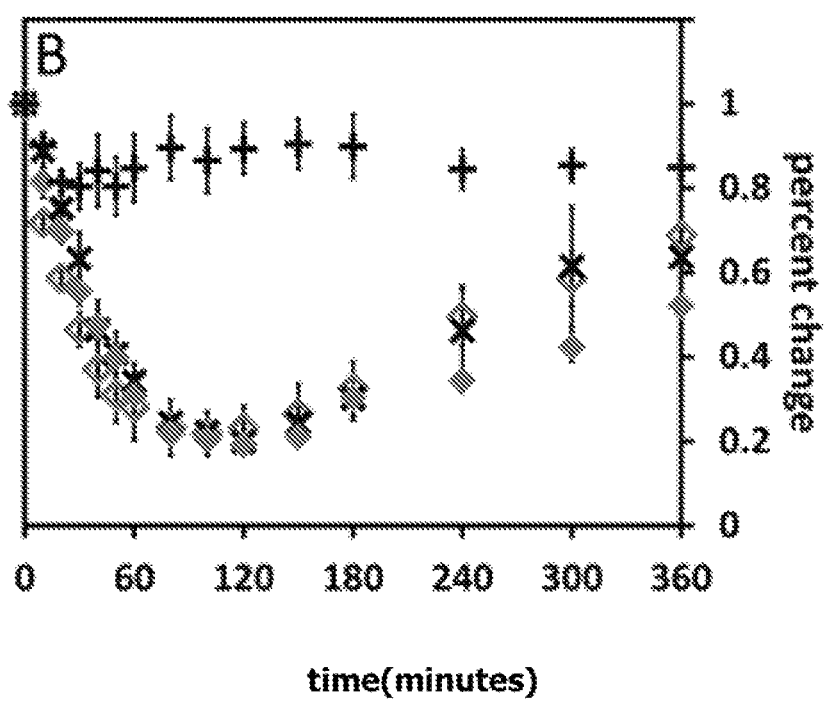
FIG. 3B is a graph of the change in blood-glucose concentrations normalized to initial blood glucose concentration over time in Sprague-Dawley rats made diabetic with streptozotocin after IV bolus injection of fresh or heat-stressed SCI not containing a fourth disulfide bridge (SCI-1 without 4SS; SEQ ID NO: 32), or fresh or heat stressed Lantus® (N=4; mean glycemia ca. 400 mg/dl). Heat stressed insulin was given gentle agitation at 95° C. for 30 min. Doses for SCIs (nominally 1 IU/rat IV) were calculated in equivalent nanomoles protein/µl. Symbols: (✚) Lantus, 95° C. for 30 min; (✖) fresh Lantus; (◇) SCI-1 without 4SS, 95° C. for 30 min; and (◆) fresh SCI-1 without 4SS.

To test the stability of single-chain insulin analogues under extreme conditions (95° C. for 30 min; FIGS. 3A and 3B), rat studies were performed following IV bolus injection to avoid potential confounding changes in SQ absorption and to enable measurement of the duration of signaling. Results are plotted in relation to blood-glucose concentration (FIG. 3A) and percent change (FIG. 3B). Whereas Lantus lost all activity after 30 min at 95° C. (✚ in FIG. 3A) versus fresh Lantus (✖ in FIG. 3A), the activity of a preliminary version of SCI-1 lacking the $4^{th}$ disulfide bridge (i.e., with Gln at position B4 and Ile at position A10 as in wild-type human insulin; SEQ ID NO: 32) was largely (but incompletely) maintained: a small reduction was observed in the activity and duration of the SCI, most noticeably between 120-420 min (heated SCI without 4SS, ◇, versus fresh SCI without 4SS, ◆). At time points 240 and 300 min, the decrement in activity was ca. 25 and 40%, respectively.

Figure 3C:
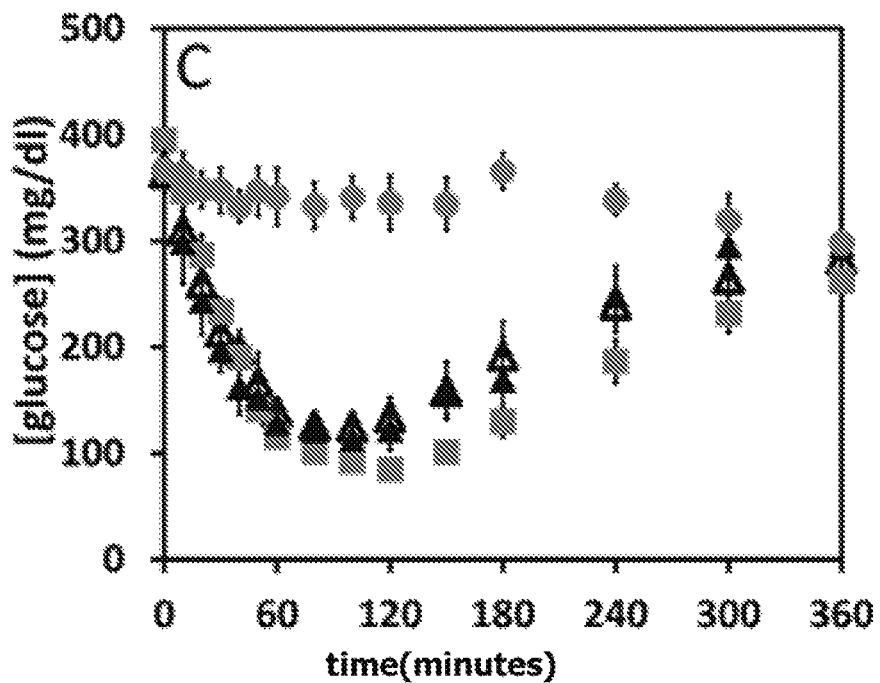
FIG. 3C is a graph of mean blood-glucose concentrations over time in Sprague-Dawley rats made diabetic with streptozotocin after IV bolus injection of fresh or heat-stressed SCIs on gentle agitation at 95° C. for 30 min (N=4; mean glycemia ca. 400 mg/dl). Symbol code: (filled triangle, ▲) fresh SCI-1; (open triangle, △) heated SCI-1; (filled square, ▩) fresh insulin lispro as positive control and (filled circle, ●) Lilly diluent (i.e., buffer only) as negative control. Doses for SCIs (nominally 1 IU/rat IV) were calculated in equivalent nanomoles protein/µl.
Figure 3D:
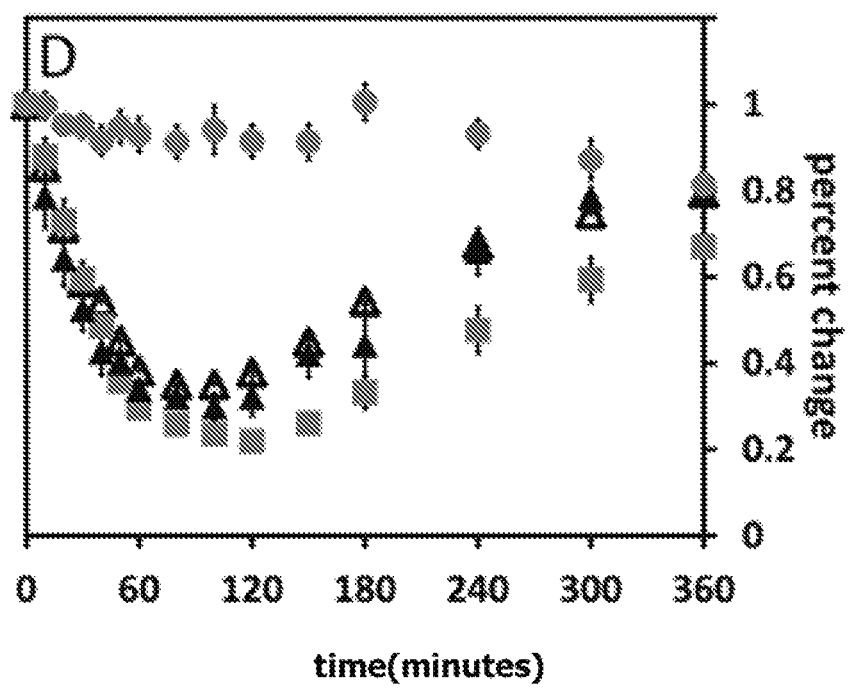
FIG. 3D is a graph of the change in blood-glucose concentrations normalized to initial blood glucose concentration over time in Sprague-Dawley rats made diabetic with streptozotocin after IV bolus injection of fresh or heat-stressed SCIs on gentle agitation at 95° C. for 30 min (N=4; mean glycemia ca. 400 mg/dl). Symbol code: (filled triangle, ▲) fresh SCI-1; (open triangle, △) heated SCI-1; (filled square, ▩) fresh insulin lispro as positive control; and (filled circle, ●) Lilly diluent (i.e., buffer only) as negative control. Doses for SCIs (nominally 1 IU/rat IV) were calculated in equivalent nanomoles protein/µl.
Figure 4:
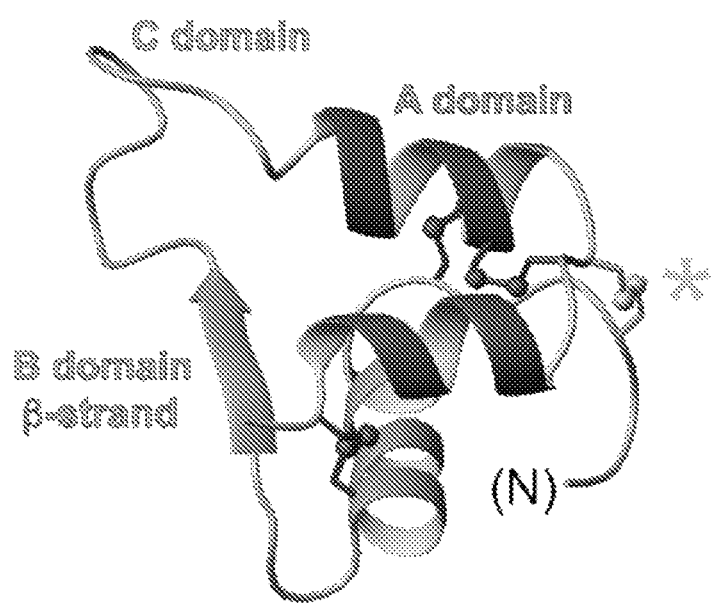
FIG. 4 provides a molecular model of a "doubly-constrained" single-chain insulin analogue, clamped at left side by an engineered 4$^{th}$ disulfide bridge (asterisk) and at the right side by a foreshortened C domain.

Such partial inactivation was entirely prevented by introduction of the engineered $4^{th}$ disulfide bridge (cystine B4-A10) to create SCI-1. This "doubly-clamped" insulin analog (stabilized at one side by cysteine B4-A10 and at the other side by the foreshortened C domain; FIG. 4) exhibited complete preservation of activity following 30 min exposure to 95° C. in solution (FIGS. 3C and 3D). We note that note that SCI-1 as a single-chain version of a 4-disulfide insulin analog exhibits normal duration of in vivo signaling on IV bolus injection (i.e., the same as insulin lispro in FIGS. 3C and 3D), in contrast to the markedly prolonged signaling exhibited by a two-chain, 4-disulfide analog as described previously. Thus, the present invention provides the surprising results providing the favorable effects of cystine B4-A10 on protein stability while mitigating the unfavorable effect of this modification, i.e., an abnormal prolongation of duration of insulin action in a diabetic animal.

Figure 5:
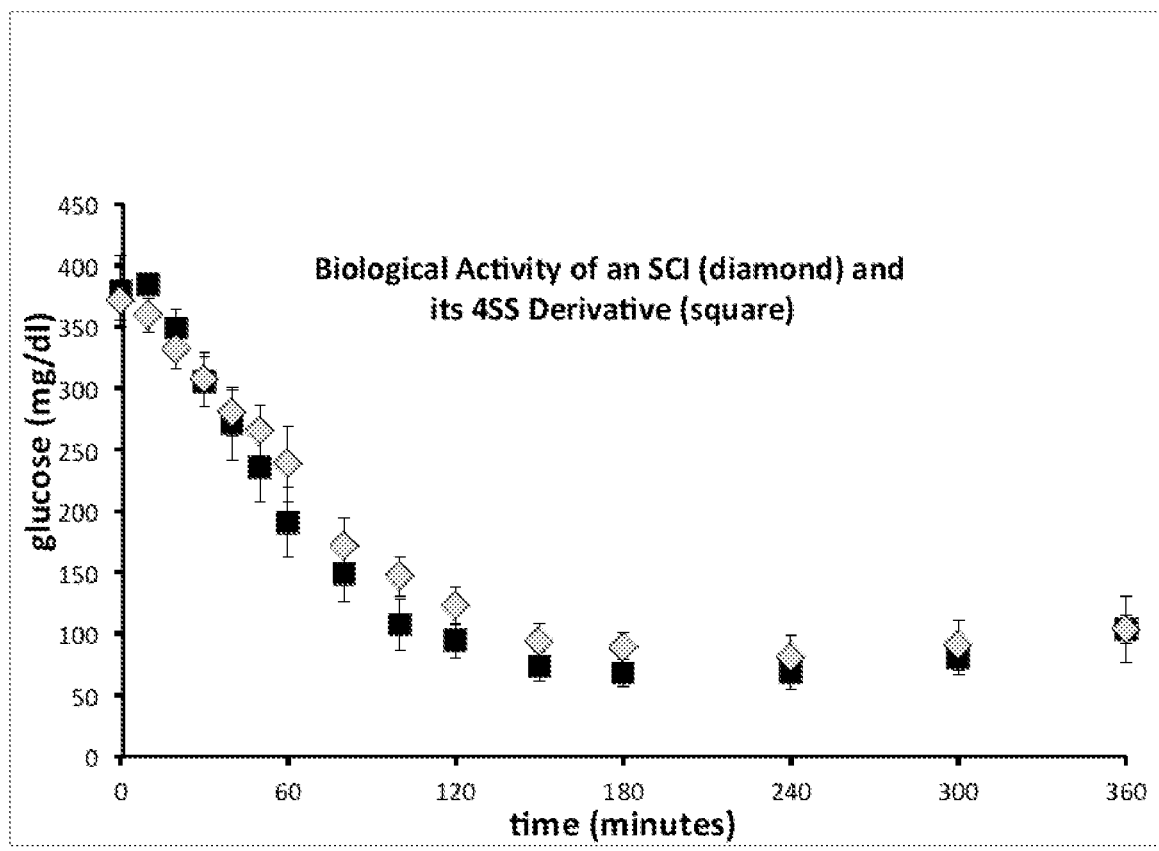
FIG. 5 is a graph showing blood glucose levels for 57 mer SCIs with (squares; 4SS 81-04; SEQ ID NO: 30) and without (diamonds; 81-04; SEQ ID NO: 31) a fourth disulfide bridge from B4 to A10, over time.

The biological activity of the 57mer SCI-2 (SEQ ID NO: 31; also noted as 4SS 81-04) was compared to a similar single chain insulin that did not have a fourth cystine bridge (noted as 81-04 herein; SEQ ID NO: 32). Providing a dose of 20 micrograms per 300 gram rat, the biological activities are essentially identical. (See FIG. 5) This demonstrates that the introduction of a fourth disulfide bridge into a single-chain insulin analogue molecule does not alter the underlying biological activity of the SCI. This is surprising in view of the prior art, which indicated that in two-chain analogs a marked prolongation of the pharmacodynamic response is observed when introducing the 4th disulfide bridge.

The receptor binding affinity of analogue 81-04 and analogue 4SS 81-04 was also determined. The affinity of 4SS 81-04 for the A isoform of the insulin receptor was determined to be 120±20 percent relative to human insulin (and may in fact be the same as wild type human insulin given the error present; data not shown). Its affinity for the B isoform of the insulin receptor is reduced by between fivefold and tenfold relative to wild type human insulin. This preference for the A isoform is similar to that of the 81-04 parent analogue. Furthermore, the affinity of 4SS 81-04 for the mitogenic IGF Type I receptor (IGF-1R) is reduced by between fivefold and tenfold relative to wild type human insulin (data not shown). Such impaired binding to IGF-1R is desirable from the perspective of potential carcinogenesis on long-term use.

A method for treating a patient with diabetes mellitus comprises administering a single-chain insulin analogue as described herein. It is another aspect of the present invention that the single-chain insulin analogues may be prepared either in yeast (*Pichia pastoris*) or subject to total chemical synthesis by native fragment ligation. The synthetic route of preparation is preferred in the case of non-standard modifications, such as D-amino-acid substitutions, halogen substitutions within the aromatic rings of Phe or Tyr, or O-linked modifications of Serine or Threonine by carbohydrates; however, it would be feasible to manufacture a subset of the single-chain analogues containing non-standard modifications by means of extended genetic-code technology or four-base codon technology. It is yet another aspect of the present invention that use of non-standard amino-acid substitutions can augment the resistance of the single-chain insulin analogue to chemical degradation or to physical degradation. We further envision the analogues of the present invention providing a method for the treatment of diabetes mellitus or the metabolic syndrome. The route of delivery of the insulin analogue is by subcutaneous injection through the use of a syringe or pen device.

A single-chain insulin analogue of the present invention may also contain other modifications, such as a halogen atom at positions B24, B25, or B26 as described more fully in U.S. Pat. No. 8,921,313, the disclosure of which is incorporated by reference herein. An insulin analogue of the present invention may also contain a foreshortened B-chain due to deletion of residues B1-B3 as described more fully in U.S. Pat. No. 9,725,493, the disclosure of which is incorporated by reference herein.

A pharmaceutical composition may comprise such insulin analogues and which may optionally include zinc. Zinc ions may be included at varying zinc ion:protein ratios, ranging from 2.2 zinc atoms per insulin analogue hexamer to 10 zinc atoms per insulin analogue hexamer. The pH of the formulation may either be in the range pH 3.0-4.5 (as a basal formulation of a pI-shifted single-chain insulin analogue) or be in the range pH 6.5-8.0 (as a prandial insulin formulation of a single-chain insulin analogue whose pI is similar to that of wild-type insulin). In either such formulation, the concentration of the insulin analogue would typically be between about 0.6-5.0 mM; concentrations up to 5 mM may be used in vial or pen; the more concentrated formulations (U-200 or higher, including in the range U-500 through U-1000) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

The amino-acid sequence of human proinsulin is provided, for comparative purposes, as SEQ ID NO: 1.

```
(human proinsulin)
                                        SEQ ID NO: 1
Phe-Val-Asn-Gln-His-Leu-Cys-Gly-Ser-His-Leu- Val-Glu-Ala-Leu-Tyr-Leu-Val-Cys-Gly-Glu-Arg- Gly-Phe-Phe-Tyr-Thr-Pro-Lys-Thr-Arg-Arg-Glu- Ala-Glu-Asp-Leu-Gln-Val-Gly-Gln-Val-Glu-Leu- Gly-Gly-Gly-Pro-Gly-Ala-Gly-Ser-Leu-Gln-Pro- Leu-Ala-Leu-Glu-Gly-Ser-Leu-Gln-Lys-Arg-Gly- Ile-Val-Glu-Gln-Cys-Cys-Thr-Ser-Ile-Cys-Ser- Leu-Tyr-Gln-Leu-Glu-Asn-Tyr-Cys-Asn
```

The amino-acid sequence of the A chain of human insulin is provided as SEQ ID NO: 2.

```
(human A chain)
                                        SEQ ID NO: 2
Gly-Ile-Val-Glu-Gln-Cys-Cys-Thr-Ser-Ile-Cys- Ser-Leu-Tyr-Gln-Leu-Glu-Asn-Tyr-Cys-Asn
```

The amino-acid sequence of the B chain of human insulin is provided as SEQ ID NO: 3.

```
(human B chain)
                                        SEQ ID NO: 3
Phe-Val-Asn-Gln-His-Leu-Cys-Gly-Ser-His-Leu- Val-Glu-Ala-Leu-Tyr-Leu-Val-Cys-Gly-Glu-Arg- Gly-Phe-Phe-Tyr-Thr-Pro-Lys-Thr
```

The amino-acid sequence of single-chain insulin analogues of the present invention are given in SEQ ID NO 4-28, containing a fourth cysteine at positions B4-A10 and corresponding to polypeptides of length 55, 57, 57, 58, 59, 60, 61, and 62, such that the SCI contains at least one other stabilizing modification at one or more of the indicated positions.

```
                                        SEQ ID NO: 4
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Xaa₁-Phe-Tyr-Thr-Pro-Xaa₂-Thr-

[foreshortened C domain]-Gly-Ile-Val-Glu-

Gln-Cys-Cys-Xaa₃-Ser-Cys-Cys-Ser-Leu-Xaa₄-

Gln-Leu-Glu-Asn-Tyr-Cys-Xaa₅
```

Where Xaa$_1$ indicates Phe, Leu, cyclohexanylalanine or a modification of Phe by a halogen atom (F, Cl or Br) at the ortho or 2-ring position; Xaa$_2$ indicts Glu, Ala, Ile, Leu, Val, Norleucine, amino-propionic acid or amino-butyric acid; where Xaa$_3$ is His, Glu, Lys, Arg, or another non-beta-branched polar or charged amino acid (i.e., Gly, Ser, Tyr, Cys, Gln, Asn, Lys, Arg, His, Asp, or Glu); where Xaa$_4$ is Tyr (as in wild-type insulin), Glu or another non-beta-branched polar or charged amino acid; and where Xaa$_5$ is Asn as in wild-type insulin or Gly, Ala, Asp, Glu or Ser. The bracketed term "[foreshortened C domain]" designates a connecting peptide domain of length 4-11 residues that contains an acidic residue at either the first (N-terminal) or second peptide position (i.e., residues 31 or 32 of the single-chain insulin analogue). Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue

```
                                        SEQ ID NO: 5
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa₁-Thr-Glu-Glu-Gly-

Pro-Arg-Arg-Gly-Ile-Val-Glu-Gln-Cys-Cys-Xaa₂-

Ser-Cys-Cys-Ser-Leu-Xaa₃-Gln-Leu-Glu-Asn-Tyr-

Cys-Xaa₄
```

Where Xaa$_1$ indicates Glu, Ala, Asp, Ile, Leu, Val, Lys, Arg, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

```
                                        SEQ ID NO: 6
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa₁-Thr-Glu-Ala-Gly-

Pro-Arg-Arg-Gly-Ile-Val-Glu-Gln-Cys-Cys-Xaa₂-

Ser-Cys-Cys-Ser-Leu-Xaa₃-Gln-Leu-Glu-Asn-Tyr-

Cys-Xaa₄
```

Where Xaa$_1$ indicates Glu, Ala, Asp, Ile, Leu, Val, Lys, Arg, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 7
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa$_1$-Thr-Ala-Glu-Gly-

Pro-Arg-Arg-Gly-Ile-Val-Glu-Gln-Cys-Cys-Xaa$_2$-

Ser-Cys-Cys-Ser-Leu-Xaa$_3$-Gln-Leu-Glu-Asn-Tyr-

Cys-Xaa$_4$

Where Xaa$_1$ indicates Glu, Ala, Asp, Ile, Leu, Val, Lys, Arg, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 8
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa$_1$-Thr-Glu-Glu-Gly-

Xaa$_2$-Arg-Arg-Gly-Ile-Val-Glu-Gln-Cys-Cys-Xaa$_3$-

Ser-Cys-Cys-Ser-Leu-Xaa$_4$-Gln-Leu-Glu-Asn-Tyr-

Cys-Xaa$_5$

Where Xaa$_1$ indicates Glu, Ala, Asp, Ile, Leu, Val, Lys, Arg, Norleucine, amino-propionic acid or amino-butyric acid; where Xaa$_2$ is Pro, Ala, Ser or Glu; where Xaa$_3$ is His, Glu, Lys, Arg, or another non-beta-branched polar or charged amino acid; where Xaa$_4$ is Tyr (as in wild-type insulin), Glu or another non-beta-branched polar or charged amino acid; and where Xaa$_5$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 9
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa$_1$-Thr-Glu-Ala-Gly-

Xaa$_2$-Arg-Arg-Gly-Ile-Val-Glu-Gln-Cys-Cys-Xaa$_3$-

Ser-Cys-Cys-Ser-Leu-Xaa$_4$-Gln-Leu-Glu-Asn-Tyr-

Cys-Xaa$_5$

Where Xaa$_1$ indicates Glu, Ala, Asp, Ile, Leu, Val, Lys, Arg, Norleucine, amino-propionic acid or amino-butyric acid; where Xaa$_2$ is Pro, Ala, Ser or Glu; where Xaa$_3$ is His, Glu, Lys, Arg, or another non-beta-branched polar or charged amino acid; where Xaa$_4$ is Tyr (as in wild-type insulin), Glu or another non-beta-branched polar or charged amino acid; and where Xaa$_5$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 10
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa$_1$-Thr-Glu-Ala-Gly-

Xaa$_2$-Xaa$_3$-Arg-Gly-Ile-Val-Glu-Gln-Cys-Cys-

Xaa$_4$-Ser-Cys-Cys-Ser-Leu-Xaa$_5$-Gln-Leu-Glu-

Asn-Tyr-Cys-Xaa$_6$

Where Xaa$_1$ indicates Glu, Ala, Asp, Ile, Leu, Val, Lys, Arg, Norleucine, amino-propionic acid or amino-butyric acid; where Xaa$_2$ is Pro, Ala, Ser or Glu; where Xaa$_3$ is Ala, Ser, Gly, Glu, Gln, or Lys; where Xaa$_4$ is His, Glu, Lys, Arg, or another non-beta-branched polar or charged amino acid; where Xaa$_5$ is Tyr (as in wild-type insulin), Glu or another non-beta-branched polar or charged amino acid; and where Xaa$_6$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 11
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Xaa$_1$-Thr-Glu-Ala-Gly-

Xaa$_2$-Arg-Xaa$_3$-Gly-Ile-Val-Glu-Gln-Cys-Cys-

Xaa$_4$-Ser-Cys-Cys-Ser-Leu-Xaa$_5$-Gln-Leu-Glu-

Asn-Tyr-Cys-Xaa$_6$

Where Xaa$_1$ indicates Glu, Ala, Asp, Ile, Leu, Val, Lys, Arg, Norleucine, amino-propionic acid or amino-butyric acid; where Xaa$_2$ is Pro, Ala, Ser or Glu; where Xaa$_3$ is Ala, Ser, Gly, Glu, Gln, or Lys; where Xaa$_4$ is His, Glu, Lys, Arg, or another non-beta-branched polar or charged amino acid; where Xaa$_5$ is Tyr (as in wild-type insulin), Glu or another non-beta-branched polar or charged amino acid; and where Xaa$_6$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 12
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Xaa$_1$-Phe-Tyr-Thr-Xaa$_2$-Pro-Thr-

[foreshortened C domain]-Gly-Ile-Val-Glu-Gln-

Cys-Cys-Xaa$_3$-Ser-Cys-Cys-Ser-Leu-Xaa$_4$-Gln-

Leu-Glu-Asn-Tyr-Cys-Xaa$_5$

Where Xaa$_1$ indicates Phe or a modification of Phe by a halogen atom (F, Cl or Br) at the ortho or 2-ring position; Xaa$_2$ indicates Gln, Glu, Ala, Asn, Asp, Ile, His, Leu, Val, ornithine, di-amino-propionic acid or di-amino-butyric acid;

where Xaa$_3$ is His, Glu, Lys, Arg, or another non-beta-branched polar or charged amino acid; where Xaa$_4$ is Tyr (as in wild-type insulin), Glu or another non-beta-branched polar or charged amino acid; and where Xaa$_5$ is Asn as in wild-type insulin or Gly, Ala, Asp, Glu or Ser. The bracketed term "[foreshortened C domain]" designates a connecting peptide domain of length 4-11 residues that contains an acidic residue at either the first (N-terminal) or second peptide position (i.e., residues 31 or 32 of the single-chain insulin analogue). Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 13
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Xaa$_1$-Pro-Thr-Glu-Glu-Gly-

Pro-Arg-Arg-Gly-Ile-Val-Glu-Gln-Cys-Cys-Xaa$_2$-

Ser-Cys-Cys-Ser-Leu-Xaa$_3$-Gln-Leu-Glu-Asn-Tyr-

Cys-Xaa$_4$

Where Xaa$_1$ (corresponding to B28) is Gln, Glu, Ala, Asn, Asp, Ile, His, Leu, Val, ornithine, di-amino-propionic acid or di-amino-butyric acid; Xaa$_2$ (corresponding to A8) is His, Glu, Lys, Arg or another non-beta branched polar or charged amino acid where Xaa$_3$ (corresponding to A14) is Tyr (as in wild-type insulin), Glu or another non-beta-branched polar or charged amino acid; and where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 14
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Xaa$_1$-Pro-Thr-Glu-Ala-Gly-

Pro-Arg-Arg-Gly-Ile-Val-Glu-Gln-Cys-Cys-Xaa$_2$-

Ser-Cys-Cys-Ser-Leu-Xaa$_3$-Gln-Leu-Glu-Asn-Tyr-

Cys-Xaa$_4$

Where Xaa$_1$ (B28) is Gln, Glu, Ala, Asn, Asp, Ile, His, Leu, Val, ornithine, di-amino-propionic acid or di-amino-butyric acid; Xaa$_2$ (A8) is His, Glu, Lys, Arg or another non-beta branched polar or charged amino acid where Xaa$_3$ (A14) is Tyr (as in wild-type insulin), Glu or another non-beta-branched polar or charged amino acid; and where Xaa$_4$ (A21) is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 15
Phe-Val-Asn-Cys-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Xaa$_1$-Pro-Thr-Ala-Glu-Gly-

Pro-Arg-Arg-Gly-Ile-Val-Glu-Gln-Cys-Cys-Xaa$_2$-

Ser-Cys-Cys-Ser-Leu-Xaa$_3$-Gln-Leu-Glu-Asn-Tyr-

Cys-Xaa$_4$

Where Xaa$_1$ (B28) is Gln, Glu, Ala, Asn, Asp, Ile, His, Leu, Val, ornithine, di-amino-propionic acid or di-amino-butyric acid; Xaa$_2$ (A8) is His, Glu, Lys, Arg or another non-beta branched polar or charged amino acid where Xaa$_3$ (A14) is Tyr (as in wild-type insulin), Glu or another non-beta-branched polar or charged amino acid; and where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 16
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Pro-Thr-Glu-Glu-Gly-Xaa$_2$-Arg-Arg-

Gly-Ile-Val-Glu-Gln-Cys-Cys-Xaa$_3$-Ser-Cys-Cys-Ser-

Leu-Xaa$_4$-Gln-Leu-Glu-Asn-Tyr-Cys-Xaa$_5$

Where Xaa$_1$ (B28) is Gln, Glu, Ala, Asn, Asp, Ile, His, Leu, Val, ornithine, di-amino-propionic acid or di-amino-butyric acid; where Xaa$_2$ is Pro or Ser; where Xaa$_3$ (A8) is His, Glu, Lys, Arg or another non-beta branched polar or charged amino acid; where Xaa$_4$ is Tyr (as in wild-type insulin), Glu or another non-beta-branched polar or charged amino acid; and where Xaa$_5$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 17
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Pro-Thr-Glu-Ala-Gly-Xaa$_2$-Arg-Arg-

Gly-Ile-Val-Glu-Gln-Cys-Cys-Xaa$_3$-Ser-Cys-Cys-Ser-

Leu-Xaa$_4$-Gln-Leu-Glu-Asn-Tyr-Cys-Xaa$_5$

Where Xaa$_1$ (B28) is Gln, Glu, Ala, Asn, Asp, Ile, His, Leu, Val, ornithine, di-amino-propionic acid or di-amino-butyric acid; where Xaa$_2$ is Pro or Ser; where Xaa$_3$(A8) is His, Glu, Lys, Arg or another non-beta branched polar or charged amino acid where Xaa$_4$ (A14) is Tyr (as in wild-type insulin), Glu or another non-beta-branched polar or charged amino acid; and where Xaa$_5$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 18
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Pro-Thr-Glu-Ala-Gly-Xaa$_2$-Xaa$_3$-Arg-

Gly-Ile-Val-Glu-Gln-Cys-Cys-Xaa$_4$-Ser-Cys-Cys-Ser-

Leu-Xaa$_5$-Gln-Leu-Glu-Asn-Tyr-Cys-Xaa$_6$

Where Xaa$_1$ is Gln, Glu, Ala, Asn, Asp, Ile, His, Leu, Val, ornithine, di-amino-propionic acid or di-amino-butyric acid; where Xaa$_2$ is Arg, Pro or Ser; where Xaa$_3$ is Arg or Ser; where Xaa$_4$ (A8) is His, Glu, Lys, Arg, or another non-beta-branched polar or charged amino acid; where Xaa$_5$ (A14) is Tyr (as in wild-type insulin), Glu or another non-beta-branched polar or charged amino acid; and where Xaa$_6$ (A21) is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 19
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Pro-Thr-Glu-Ala-Gly-Xaa$_2$-Arg-Xaa$_3$-

Gly-Ile-Val-Glu-Gln-Cys-Cys-Xaa$_4$-Ser-Cys-Cys-Ser-

Leu-Xaa$_5$-Gln-Leu-Glu-Asn-Tyr-Cys-Xaa$_6$

Where Xaa$_1$ (B28) is Gln, Glu, Ala, Asn, Asp, Ile, His, Leu, Val, ornithine, di-amino-propionic acid or di-amino-butyric acid; where Xaa$_2$ is Arg, Pro or Ser; where Xaa$_3$ is Arg, Pro or Ser; where Xaa$_4$ (A8) is His, Glu, Lys, Arg, or another non-beta-branched polar or charged amino acid; where Xaa$_5$ (A14) is Tyr (as in wild-type insulin), Glu or another non-beta-branched polar or charged amino acid; and where Xaa$_6$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 20
Phe-Val-Asn-Cys-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Pro-Xaa$_2$-Thr-Glu-Glu-Gly-Ser-Arg-Arg-

Ser-Arg-Gly-Ile-Val-Glu-Gln-Cys-Cys-Xaa$_3$-Ser-Cys-

Cys-Ser-Leu-Xaa$_4$-Gln-Leu-Glu-Asn-Tyr-Cys-Xaa$_5$

Where Xaa$_1$ indicates Phe, Leu, cyclohexanylalanine or a modification of Phe by a halogen atom (F, Cl or Br) at the ortho or 2-ring position; Xaa$_2$ indicates Arg or Lys; where Xaa$_3$ is His, Lys, Arg, or another non-beta-branched polar or basic acid; where Xaa$_4$ is Tyr (as in wild-type insulin), Glu or another non-beta-branched polar or charged amino acid; and optionally where Xaa$_5$ is Asn as in wild-type insulin or Gly, Ala, Asp, Glu or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 21
Phe-Val-Asn-Cys-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Pro-Arg-Thr-Glu-Glu-Gly-Ser-Arg-Arg-

Ser-Arg-Gly-Ile-Val-Glu-Gln-Cys-Cys-Arg-Ser-Cys-

Cys-Ser-Leu-Tyr-Gln-Leu-Glu-Asn-Tyr-Cys-Gly

Where Xaa$_1$ indicates Phe, Leu, cyclohexanylalanine or a modification of Phe by a halogen atom (F, Cl or Br) at the ortho or 2-ring position; Xaa$_2$ indicates Arg or Lys; where Xaa$_3$ is His, Lys, Arg, or another non-beta-branched polar or basic acid; where Xaa$_4$ is Tyr (as in wild-type insulin), Glu or another non-beta-branched polar or charged amino acid; and optionally where Xaa$_5$ is Asn as in wild-type insulin or Gly, Ala, Asp, Glu or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 22
Phe-Val-Asn-Cys-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Pro-Arg-Thr-Glu-Ala-Gly-Ser-Arg-Arg-

Ser-Arg-Gly-Ile-Val-Glu-Gln-Cys-Cys-Arg-Ser-Cys-

Cys-Ser-Leu-Tyr-Gln-Leu-Glu-Asn-Tyr-Cys-Gly

Where Xaa$_1$ indicates Phe, Leu, cyclohexanylalanine or a modification of Phe by a halogen atom (F, Cl or Br) at the ortho or 2-ring position; Xaa$_2$ indicates Arg or Lys; where Xaa$_3$ is His, Lys, Arg, or another non-beta-branched polar or basic acid; where Xaa$_4$ is Tyr (as in wild-type insulin), Glu or another non-beta-branched polar or charged amino acid; and optionally where Xaa$_5$ is Asn as in wild-type insulin or Gly, Ala, Asp, Glu or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 23
Phe-Val-Asn-Cys-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Pro-Arg-Thr-Ala-Glu-Gly-Ser-Arg-Arg-

Ser-Arg-Gly-Ile-Val-Glu-Gln-Cys-Cys-Arg-Ser-Cys-

Cys-Ser-Leu-Tyr-Gln-Leu-Glu-Asn-Tyr-Cys-Gly

Where Xaa$_1$ indicates Phe, Leu, cyclohexanylalanine or a modification of Phe by a halogen atom (F, Cl or Br) at the ortho or 2-ring position; Xaa$_2$ indicates Arg or Lys; where Xaa$_3$ is His, Lys, Arg, or another non-beta-branched polar or basic acid; where Xaa$_4$ is Tyr (as in wild-type insulin), Glu or another non-beta-branched polar or charged amino acid; and optionally where Xaa$_5$ is Asn as in wild-type insulin or Gly, Ala, Asp, Glu or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 24
Phe-Val-Asn-Cys-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Pro-Arg-Thr-Glu-Glu-Gly-Pro-Arg-Arg-

Ser-Arg-Gly-Ile-Val-Glu-Gln-Cys-Cys-Arg-Ser-Cys-

Cys-Ser-Leu-Tyr-Gln-Leu-Glu-Asn-Tyr-Cys-Gly

Where Xaa$_1$ indicates Phe, Leu, cyclohexanylalanine or a modification of Phe by a halogen atom (F, Cl or Br) at the ortho or 2-ring position; Xaa$_2$ indicates Arg or Lys; where Xaa$_3$ is His, Lys, Arg, or another non-beta-branched polar or basic acid; where Xaa$_4$ is Tyr (as in wild-type insulin), Glu or another non-beta-branched polar or charged amino acid; and optionally where Xaa$_5$ is Asn as in wild-type insulin or Gly, Ala, Asp, Glu or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 25
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_1$-Thr-Glu-Glu-Arg-Arg-Gly-Ile-

Val-Glu-Gln-Cys-Cys-Xaa$_2$-Ser-Cys-Cys-Ser-Leu-Xaa$_3$-

Gln-Leu-Glu-Asn-Tyr-Cys-Xaa$_4$

Where Xaa$_1$ indicates Glu, Ala, Ile, Leu, Val, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and optionally where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 26
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_1$-Thr-Glu-Glu-Gly-Arg-Arg-Gly-

Ile-Val-Glu-Gln-Cys-Cys-Xaa$_2$-Ser-Cys-Cys-Ser-Leu-

Xaa$_3$-Gln-Leu-Glu-Asn-Tyr-Cys-Xaa$_4$

Where Xaa$_1$ indicates Glu, Ala, Ile, Leu, Val, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and optionally where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 27
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_1$-Thr-Glu-Glu-Ala-Arg-Arg-Gly-

Ile-Val-Glu-Gln-Cys-Cys-Xaa$_2$-Ser-Cys-Cys-Ser-Leu-

Xaa$_3$-Gln-Leu-Glu-Asn-Tyr-Cys-Xaa$_4$

Where Xaa$_1$ indicates Glu, Ala, Ile, Leu, Val, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and optionally where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 28
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_1$-Thr-Glu-Glu-Ser-Arg-Arg-Gly-

Ile-Val-Glu-Gln-Cys-Cys-Xaa$_2$-Ser-Cys-Cys-Ser-Leu-

Xaa$_3$-Gln-Leu-Glu-Asn-Tyr-Cys-Xaa$_4$

Where Xaa$_1$ indicates Glu, Ala, Ile, Leu, Val, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and optionally where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

SEQ ID NO: 29
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_1$-Thr-Glu-Glu-Pro-Arg-Arg-Gly-

Ile-Val-Glu-Gln-Cys-Cys-Xaa$_2$-Ser-Cys-Cys-Ser-Leu-

Xaa$_3$-Gln-Leu-Glu-Asn-Tyr-Cys-Xaa$_4$

Where Xaa$_1$ indicates Glu, Ala, Ile, Leu, Val, Norleucine, amino-propionic acid or amino-butyric acid; where Xaa$_2$ is His, Glu, Lys, Arg, or another non-beta-branched polar or charged amino acid; where Xaa$_3$ is Tyr (as in wild-type insulin), Glu or another non-beta-branched polar or charged amino acid; and optionally where Xaa$_4$ is Gly, Glu, Ala, Asn, Asp or Ser. Optionally, Phe$^{B1}$ may be deleted to yield a des-B1 analogue, Phe$^{B1}$ and Val$^{B2}$ both may be omitted to yield a des-[B1, B2] analogue, or Phe$^{B1}$, Val$^{B2}$ and Asn$^{A3}$ may all deleted to yield a des-[B1-B3] single-chain analogue.

(SCI-1, 59-mer)

SEQ ID NO: 30

Phe-Val-Asn-Cys-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Arg-Thr-Glu-Glu-Gly-Ser-Arg-Arg-
Ser-Arg-Gly-Ile-Val-Glu-Gln-Cys-Cys-Arg-Ser-Cys-
Cys-Ser-Leu-Tyr-Gln-Leu-Glu-Asn-Tyr-Cys-Asn (SCI-2; 4SS 81-04; 57-mer)

SEQ ID NO: 31

Phe-Val-Asn-Cys-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Asp-Pro-Thr-Glu-Glu-Gly-Pro-Arg-Arg-
Gly-Ile-Val-Glu-Gln-Cys-Cys-His-Ser-Cys-Cys-Ser-
Leu-Glu-Gln-Leu-Glu-Asn-Tyr-Cys-Asn (81-04; 57-mer)

SEQ ID NO: 32

Phe-Val-Asn-Gln-His-Leu-Cys-Gly-Ser-His-Leu-Val-

-continued

Glu-Ala-Leu-Tyr-Leu-Val-Cys-Gly-Glu-Arg-Gly-Phe-
Phe-Tyr-Thr-Asp-Pro-Thr-Glu-Glu-Gly-Pro-Arg-Arg-
Gly-Ile-Val-Glu-Gln-Cys-Cys-His-Ser-Ile-Cys-Ser-
Leu-Glu-Gln-Leu-Glu-Asn-Tyr-Cys-Asn

Based upon the foregoing disclosure, it should now be apparent that the enhanced stability conferred by an engineered 4$^{th}$ disulfide bridge can be made compatible with unperturbed duration of insulin signaling through the co-engineering of a foreshortened C domain. The resulting single-chain insulin analogues provided will carry out the objects set forth hereinabove. Namely, these modified proteins exhibit enhanced resistance to fibrillation while retaining desirable pharmacokinetic features (conferring rapid or prolonged rates of absorption from a subcutaneous depot as may be therapeutically desired) and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

What is claimed is:

1. A single-chain insulin analogue comprising a B-chain insulin polypeptide sequence connected to an A-chain insulin polypeptide sequence by a C-domain polypeptide sequence; wherein the B-chain insulin polypeptide sequence contains a Cysteine substitution at position B4 relative to the sequence of wild type insulin; wherein the A-chain insulin polypeptide sequence contains a Cysteine substitution at position A10 relative to the sequence of wild type insulin and wherein the C-domain polypeptide sequence is 4 to 11 amino acids long.

2. The single-chain insulin analogue of claim 1, wherein the C-domain polypeptide sequence comprises an N-terminal acidic element and a C-terminal basic element.

3. The single-chain insulin analogue of claim 1, wherein the analogue comprises any one of SEQ ID NOS: 4-31.

4. The single-chain insulin analogue of claim 3, wherein the C-domain polypeptide begins with Glu-Glu.

5. The single-chain insulin of claim 4, wherein the C-domain polypeptide comprises residues 31-36 of SEQ ID NO: 31.

6. The single-chain insulin of claim 5, wherein the analogue comprises SEQ ID NO: 31.

7. The single-chain insulin of claim 4, wherein the C-domain polypeptide comprises residues 31-38 of SEQ ID NO: 30.

8. The single-chain insulin of claim 7, wherein the analogue comprises SEQ ID NO: 30.

9. The single-chain insulin of claim 3, comprising SEQ ID NO: 8.

10. The single-chain insulin analogue of claim 3, wherein the C-domain polypeptide ends with Arg-Arg.

11. The single-chain insulin analogue of claim 10, wherein the analogue is selected from the group consisting of SEQ ID NOs: 5-9, 13-19, 25-29 and 31.

12. The single-chain insulin analogue of claim 3, wherein the C-domain polypeptide ends with Arg-Arg-Ser-Arg.

13. The single-chain insulin analogue of claim 12, wherein the analogue is selected from the group consisting of SEQ ID NOs: 20-24 and 30.

14. A method of lowering the blood sugar of a patient, in need thereof the method comprising administering a physiologically effective amount of a single-chain insulin analogue or a physiologically acceptable salt thereof to the patient, wherein the single-chain insulin analogue comprises a B-chain insulin polypeptide sequence connected to an A-chain insulin polypeptide sequence by a C-domain polypeptide sequence; wherein the B-chain insulin polypeptide sequence contains a Cysteine substitution at position B4 relative to the sequence of wild type insulin; wherein the A-chain insulin polypeptide sequence contains a Cysteine substitution at position A10 relative to the sequence of wild type insulin and wherein the C-domain polypeptide sequence is 4 to 11 amino acids long.

15. The method of claim 14, wherein the analogue comprises any one of SEQ ID NOS: 4-31.

16. The method of claim 14, wherein the C-domain polypeptide begins with Glu-Glu.

17. The method of claim 16, wherein the C-domain polypeptide comprises residues 31-36 of SEQ ID NO: 31.

18. The method of claim 17, wherein the analogue comprises SEQ ID NO: 31.

* * * * *